United States Patent
Lee et al.

(10) Patent No.: US 10,751,500 B2
(45) Date of Patent: Aug. 25, 2020

(54) APPARATUS AND METHOD FOR OXYGEN DELIVERY

(71) Applicant: OXUS CO., LTD., Gyeonggi-do (KR)

(72) Inventors: Tae-Soo Lee, Gyeonggi-do (KR); Yoon-Sun Choi, Seoul (KR); Seung-Kwon Oh, Gyeonggi-do (KR); Gil-Jun Lee, Gyeonggi-do (KR)

(73) Assignee: OXUS CO., LTD., Gyeonggi-do (KR)

( * ) Notice: Subject to any disclaimer, the term of this patent is extended or adjusted under 35 U.S.C. 154(b) by 376 days.

(21) Appl. No.: 15/893,566

(22) Filed: Feb. 9, 2018

(65) Prior Publication Data

US 2018/0177972 A1 Jun. 28, 2018

Related U.S. Application Data

(63) Continuation-in-part of application No. 14/361,676, filed as application No. PCT/KR2011/010079 on Dec. 26, 2011, now abandoned.

(30) Foreign Application Priority Data

Nov. 30, 2011 (KR) ........................ 10-2011-0127062

(51) Int. Cl.
*A61M 16/20* (2006.01)
*A61M 16/10* (2006.01)
(Continued)

(52) U.S. Cl.
CPC ...... *A61M 16/203* (2014.02); *A61M 16/0677* (2014.02); *A61M 16/1005* (2014.02);
(Continued)

(58) Field of Classification Search
CPC .............. A61M 16/00; A61M 16/0051; A61M 16/1005; A61M 16/0003; A61M 16/0677;
(Continued)

(56) References Cited

U.S. PATENT DOCUMENTS 4,648,395 A * 3/1987 Sato .................. A61M 16/0677
128/204.23
4,681,099 A * 7/1987 Sato .................... A61M 16/024
128/204.23
(Continued)

FOREIGN PATENT DOCUMENTS

| JP | 08-019615 A | 1/1996 |
|---|---|---|
| JP | 4796918 B2 | 10/2011 |
| KR | 10-1029456 B1 | 4/2011 |

*Primary Examiner* — Tu A Vo
(74) *Attorney, Agent, or Firm* — Rabin & Berdo, P.C.

(57) ABSTRACT

An oxygen delivery method for delivering oxygen stored in an oxygen tank to a recipient according to an embodiment of the present invention includes: receiving a prescription flow that is an oxygen delivery flow prescribed to the recipient; receiving a saving ratio, the saving ratio being input by the recipient and being a ratio of a prescription flow and an average delivery flow; selecting an oxygen delivery mode among a plurality of preset oxygen delivery modes based on the saving ratio; detecting a breathing pressure of the recipient; and controlling an oxygen delivery flow to the recipient based on the prescription flow, the saving ratio and detected breathing pressure.

13 Claims, 6 Drawing Sheets

(51) Int. Cl.
*A61M 16/06* (2006.01)
*A61M 16/00* (2006.01)

(52) U.S. Cl.
CPC ... *A61M 16/024* (2017.08); *A61M 2016/0021* (2013.01); *A61M 2016/0027* (2013.01); *A61M 2202/0208* (2013.01); *A61M 2205/502* (2013.01)

(58) Field of Classification Search
CPC .............. A61M 16/202; A61M 16/203; A61M 2205/50; A61M 2202/0208; A61M 2016/0021; A61M 2016/0027–0042; A61M 16/20; A61M 16/201; A61M 16/204; A61M 16/0006; A61M 16/0009; A61M 16/0012; A61M 2016/0015; A61M 2016/0018; A61M 2016/003; A61M 2016/0033; A61M 2016/0036; A61M 2016/0039; A61M 16/0057; A61M 16/006; A61M 16/0063; A61M 16/0066; A61M 16/101; A61M 2202/0007; A61M 2202/02; A61M 2205/33; A61M 2205/3331; A61M 2205/3334; A61M 2205/3337; A61M 2205/3341; A62B 7/04; A62B 7/00; A62B 7/02; A62B 7/06; A62B 7/08

See application file for complete search history.

(56) References Cited

U.S. PATENT DOCUMENTS

| | | | |
|---|---|---|---|
| 4,971,049 A | | 11/1990 | Rotariu et al. |
| 5,603,315 A | * | 2/1997 | Sasso, Jr. .......... A61M 16/0677 128/204.18 |
| 2002/0038656 A1 | * | 4/2002 | Yagi .................... A61M 16/101 128/204.23 |
| 2006/0048781 A1 | * | 3/2006 | Nawata ............... A61M 16/101 128/204.23 |
| 2006/0070624 A1 | | 4/2006 | Kane et al. |
| 2008/0127975 A1 | | 6/2008 | Lirsch et al. |
| 2008/0178880 A1 | | 7/2008 | Christopher et al. |
| 2009/0126731 A1 | | 5/2009 | Dunsmore et al. |
| 2011/0154986 A1 | | 6/2011 | Lee et al. |

* cited by examiner

APPARATUS AND METHOD FOR OXYGEN DELIVERY

TECHNICAL FIELD

The present invention relates to an apparatus and method for oxygen delivery.

BACKGROUND ART

With the rapid aging of population, air pollution and smoking, patients of lung diseases and respiratory diseases are rapidly increasing. An oxygen delivery apparatus is widely used in respiratory assistance for the patients of lung diseases and respiratory diseases in breathing. In particular, oxygen therapy is almost the only effective way for treatment of chronic obstructive pulmonary disease (COPD).

The oxygen therapy means a treatment for preventing saturation of oxygen in blood from being lowered by facilitating an increase in the fraction of inspired oxygen ($FIO_2$) in lung by delivering oxygen of a higher concentration than atmospheric oxygen to patients of lung diseases. In the conventional oxygen therapy, a continuous flow oxygen (CFO) method and a demand oxygen delivery (DOD) method are used.

In the CFO method, a constant amount of oxygen is continuously supplied to a patient. According to the CFO method, since oxygen delivery is performed even when oxygen is not required by the patient, the oxygen may be considerably squandered. In the DOD method, a high flow oxygen stream is supplied to a patient for a short time by sensing a patient's inhale time. According to the DOD method, a considerable oxygen saving effect can be achieved. However, the patient may feel uncomfortable due to abruptly induced oxygen, making it difficult to employ the DOD method for a long time or in patient's sleep.

DISCLOSURE

Technical Problems

The present invention has been made in an effort to solve the problems of the prior art, and it is an object of the present invention to provide an apparatus and method for oxygen delivery, which can implement an oxygen delivery pattern capable of minimizing patient's objection or inconvenience while reducing oxygen squandering.

Technical Solution

An oxygen delivery apparatus according to an exemplary embodiment of the present invention includes: an oxygen tank storing oxygen; an outlet valve unit configured to include a variable flow valve capable of variably controlling an amount of oxygen delivered from the oxygen tank to a recipient; a pressure sensor adapted to detect a breathing pressure of the recipient and outputting a pressure signal corresponding to the breathing pressure; and a control unit controlling an operation of the outlet valve unit based on the pressure signal from the pressure sensor to control the amount of oxygen delivered to the recipient. The control unit selects an oxygen delivery mode among a plurality of preset oxygen delivery modes based on a saving ratio (SR), the saving ratio being input by the recipient and being a ratio of a prescription flow ($Q_p$) and an average delivery flow ($Q_s$), and controls the outlet valve unit based on the pressure signal and the selected oxygen delivery mode.

The control unit may select the oxygen delivery mode depending on comparison of the input saving ratio to a plurality of preset saving ratios.

In an oxygen delivery method using an oxygen delivery apparatus according to an exemplary embodiment of the present invention, the oxygen delivery apparatus includes: an oxygen tank storing oxygen; an outlet valve unit configured to include a variable flow valve capable of variably controlling an amount of oxygen delivered from the oxygen tank to a recipient; a pressure sensor adapted to detect a breathing pressure of the recipient and outputting a pressure signal corresponding to the breathing pressure; and a control unit controlling an operation of the outlet valve unit based on the pressure signal from the pressure sensor to control the amount of oxygen delivered to the recipient. An oxygen delivery mode is selected among a plurality of preset oxygen delivery modes based on a saving ratio (SR), the saving ratio being input by the recipient and being a ratio of a prescription flow ($Q_p$) and an average delivery flow ($Q_s$), and the outlet valve unit is controlled based on the pressure signal and the selected oxygen delivery mode. The oxygen delivery mode is selected depending on comparison of the input saving ratio to a plurality of preset saving ratios.

The plurality of preset oxygen delivery modes may include a first oxygen delivery mode, a second oxygen delivery mode and a third oxygen delivery mode, wherein the plurality of preset saving ratios comprise a first preset saving ratio and a second preset saving ratio which is greater than the first preset saving ratio, and wherein the first oxygen delivery mode is selected if the input saving ratio is less than the first preset saving ratio, the second oxygen delivery mode is selected if the input saving ratio is between the first preset saving ratio and the second preset saving ratio, and the third oxygen delivery mode is selected if the input saving ratio is greater than the second preset saving ratio.

In the first oxygen delivery mode a first control process, a second control process and a third control process may be sequentially performed. The first control process may be performed to control the outlet valve unit for making an oxygen delivery flow become equal to a base flow at highest-inhalation pressure time in a state in which the outlet valve unit is controlled to deliver the prescription flow during inhalation and to control the state to be maintained up to an exhalation start time detected in real time. The second control process may be performed to control the outlet valve unit to allow the oxygen delivery flow to gradually increase from the base flow up to the prescription flow for a period from the exhalation start time to the next inhalation start time. The third control process may be performed to control the outlet valve unit to deliver the prescription flow from the next inhalation start time to a next highest-inhalation pressure time.

In the second oxygen delivery mode a first control process, a second control process and a third control process may be sequentially performed. The first control process may be performed to control the outlet valve unit to prevent an oxygen delivery at a highest-inhalation pressure time detected in real time in a state in which the outlet valve unit is controlled to deliver the prescription flow and to control the state to be maintained up to a delivery resumption time. The second control process may be performed to control the outlet valve unit to allow the oxygen delivery flow to gradually increase from zero up to the prescription flow for a period from the oxygen delivery resumption time to a next inhalation start time. The third control process may be performed to control the outlet valve unit to deliver the prescription flow from the next inhalation start time to a next highest-inhalation pressure time.

The oxygen delivery apparatus may further include an on-off valve that delivers oxygen having a pulse shape flow profile, and in the third oxygen delivery mode a first control process, a second control process and a third control process may be sequentially performed. The first control process may be performed to control the outlet valve unit to prevent an oxygen delivery up to an oxygen delivery resumption time during exhalation. The second control process may be performed to control the outlet valve unit to gradually increase the oxygen delivery flow up to a target oxygen flow for a period from the oxygen delivery resumption time to a next inhalation start time. The third control process may be performed to control the outlet valve unit to deliver oxygen having a pulse shape flow profile at the next inhalation start time.

An oxygen delivery method for delivering oxygen stored in an oxygen tank to a recipient according to an embodiment of the present invention includes: receiving a prescription flow ($Q_p$) that is an oxygen delivery flow prescribed to the recipient; receiving a saving ratio (SR), the saving ratio being input by the recipient and being a ratio of a prescription flow ($Q_p$) and an average delivery flow ($Q_s$); selecting an oxygen delivery mode among a plurality of preset oxygen delivery modes based on the saving ratio; detecting a breathing pressure of the recipient; and controlling an oxygen delivery flow to the recipient based on the prescription flow ($Q_p$), the saving ratio (SR) and detected breathing pressure.

The oxygen delivery mode may be selected depending on comparison of the input saving ratio to a plurality of preset saving ratios.

The plurality of preset oxygen delivery modes may include a first oxygen delivery mode, a second oxygen delivery mode and a third oxygen delivery mode. The plurality of preset saving ratios may include a first preset saving ratio and a second preset saving ratio which is greater than the first preset saving ratio. The first oxygen delivery mode may be selected if the input saving ratio is less than the first preset saving ratio, the second oxygen delivery mode may be selected if the input saving ratio is between the first preset saving ratio and the second preset saving ratio, and the third oxygen delivery mode may be selected if the input saving ratio is greater than the second preset saving ratio.

In the first oxygen delivery mode a first control process, a second control process and a third control process may be sequentially performed. The first control process may be performed to make an oxygen delivery flow become equal to a base flow at highest-inhalation pressure time in a state in which the prescription flow is delivered during inhalation and to control the state to be maintained up to an exhalation start time detected in real time. The second control process may be performed to allow the oxygen delivery flow to gradually increase from the base flow up to the prescription flow for a period from the exhalation start time to the next inhalation start time. The third control process may be performed to deliver the prescription flow from the next inhalation start time to a next highest-inhalation pressure time.

In the second oxygen delivery mode a first control process, a second control process and a third control process may be sequentially performed. The first control process may be performed to prevent an oxygen delivery at a highest-inhalation pressure time detected in real time in a state in which the prescription flow is delivered and to control the state to be maintained up to a delivery resumption time. The second control process may be performed to allow the oxygen delivery flow to gradually increase from zero up to the prescription flow for a period from the oxygen delivery resumption time to a next inhalation start time. The third control process may be performed to deliver the prescription flow from the next inhalation start time to a next highest-inhalation pressure time.

In the third oxygen delivery mode a first control process, a second control process and a third control process may be sequentially performed. The first control process may be performed to prevent an oxygen delivery up to an oxygen delivery resumption time during exhalation. The second control process may be performed to gradually increase the oxygen delivery flow up to a target oxygen flow for a period from the oxygen delivery resumption time to a next inhalation start time. The third control process may be performed to deliver oxygen having a pulse shape flow profile at the next inhalation start time.

Advantageous Effects

According to the apparatus and method for oxygen delivery of the present invention, it is possible to implement an oxygen delivery pattern capable of minimizing patient's objection or inconvenience while reducing oxygen squandering which can implement. In addition, reliability in oxygen delivery can be secured by maintaining $FIO_2$ equivalency in lung.

DETAILED DESCRIPTION

Hereinafter, preferred embodiments of the present invention will now be described in detail with reference to the accompanying drawings.

Figure 1:
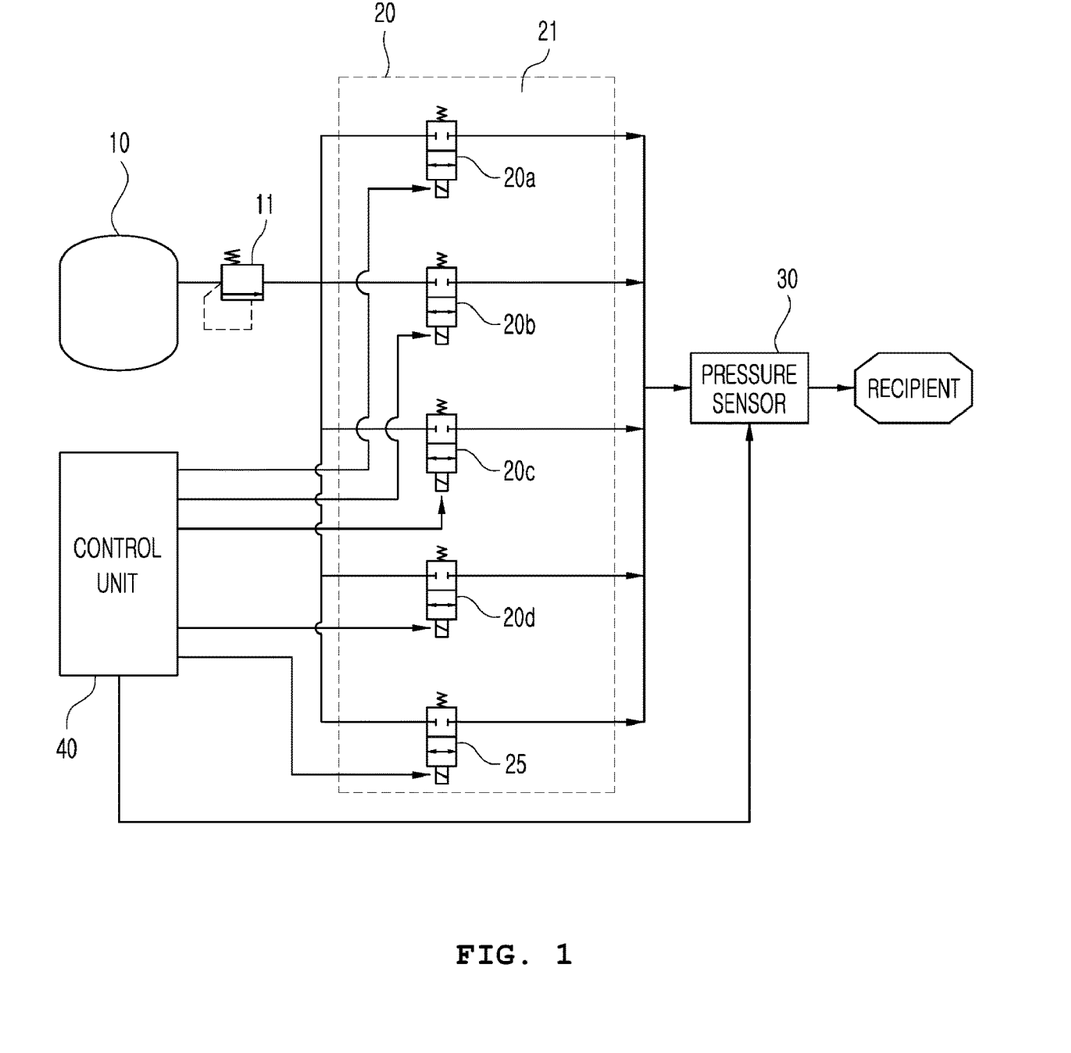
FIG. 1 is a schematic block diagram of an oxygen delivery apparatus according to one embodiment of the present invention.
Figure 2:
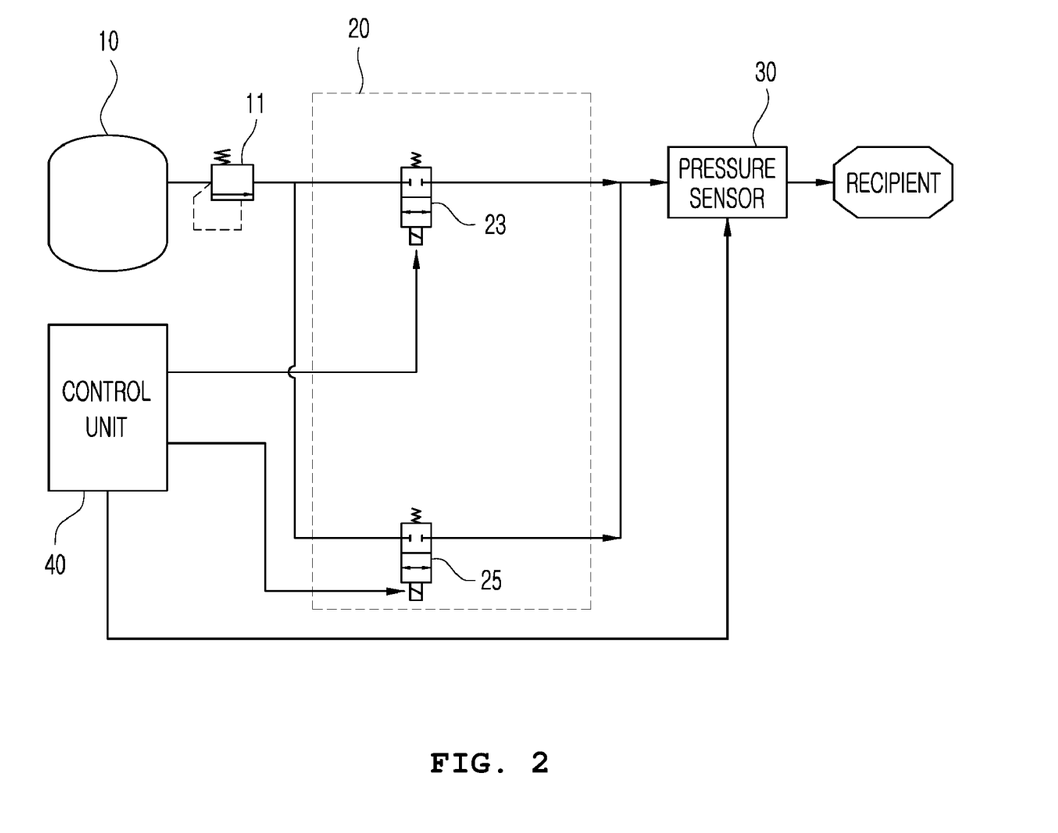
FIG. 2 is a schematic block diagram of an oxygen delivery apparatus according to another embodiment of the present invention.

Referring to FIGS. 1 and 2, an oxygen delivery apparatus according to an embodiment of the present invention includes an oxygen tank 10 for delivering oxygen.

The oxygen tank 10 stores oxygen to be delivered to a recipient (for example, a patient). When necessary, a pressure regulator 11 being capable of regulating a pressure of oxygen which is being discharged may be disposed at an outlet of the oxygen tank 10.

Meanwhile, the oxygen delivery apparatus includes an outlet valve unit 20 for controlling the oxygen flow delivered from the oxygen tank 10 to the recipient.

Figure 3:
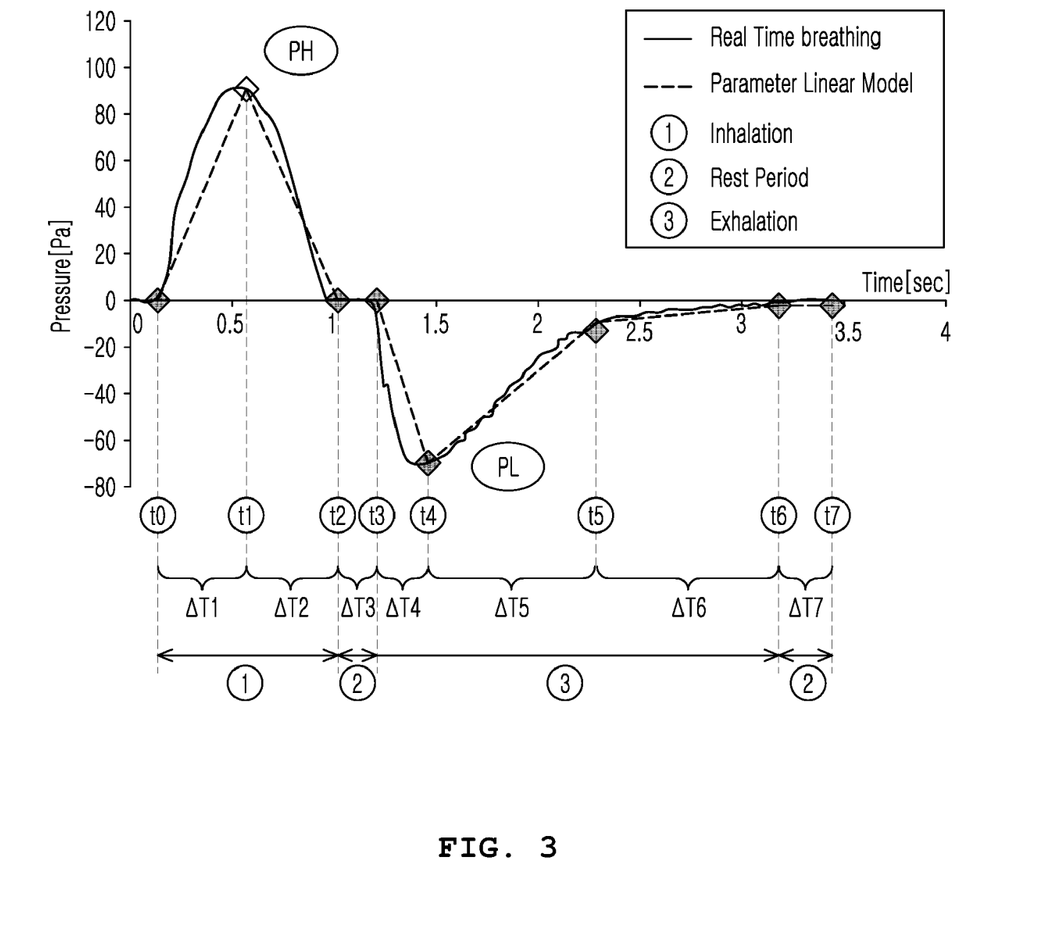
FIG. 3 is a view for illustrating an estimating method of a breathing pattern in an oxygen delivery method according to an embodiment of the present invention.

Referring to FIGS. 2 and 3, the outlet valve unit 20 may include variable flow valves 21 and 23 capable of variably controlling the amount of oxygen delivered to the recipient.

Referring to FIG. 1, according to one embodiment of the present invention, the variable flow valve 21 may be constituted by a combination of a plurality of on-off valves 21a, 21b, 21c and 21d. For example, the plurality of on-off valves 21*a*, 21*b*, 21*c* and 21*d* may be valves allowing oxygen to flow at different flow rates when they are on. One or more of the plurality of on-off valves 21*a*, 21*b*, 21*c* and 21*d* may be turned on to variably control the oxygen flow delivered to the recipient.

Meanwhile, referring to FIG. 2, the variable flow valve 23 may be implemented by a proportional control valve. The proportional control valve 23 is a valve which can easily control the flow of oxygen in response to an input control signal.

Further, according to another embodiment of the present invention, the outlet valve unit 20 may further include an on-off valve 25 supplying oxygen having a pulse-like flow profile.

The variable flow valves 21 and 23 may be used when oxygen having a variable flow profile is delivered, and the on-off valve 25 may be used to deliver the oxygen having a pulse-like flow profile.

A pressure sensor 30 detects a breathing pressure of the recipient and outputs a pressure signal. The pressure sensor 30 may be installed at a place that can be exposed to the breathing pressure of the recipient, for example, may be installed in a conduit for delivering oxygen to the recipient.

A control unit 40 controls the operation of the outlet valve unit 20 to adjust the amount of oxygen delivered to the recipient on the basis of the pressure signal of the pressure sensor 30. To this end, the control unit 40 may be electrically connected to the pressure sensor 30 so as to receive the signal from the pressure sensor 30. In addition, the control unit 40 may be electrically connected to the outlet valve unit 20 so as to output a control signal for controlling the outlet valve unit 20.

The control unit 40 may include a microprocessor, a memory, and associated hardware and software. The microprocessor may be programmed to execute the oxygen delivery method according to an embodiment of the present invention, which will later be described, and the memory may store various kinds of data for executing the oxygen delivery method.

In addition, as shown in FIGS. 1 and 2, the respective valves constituting the outlet valve unit 20 may be connected to the oxygen tank 10 and the recipient by a connecting conduit, the oxygen may be selectively delivered from the oxygen tank 10 to the recipient through the connecting conduit according to the operation of the outlet valve unit 20.

Hereinafter, specific operation mechanism of the oxygen delivery apparatus according to an embodiment of the present invention and an oxygen delivery method according to an embodiment of the present invention, which may be executed by the oxygen delivery apparatus, will be described in detail with reference to the accompanying drawings.

According to the embodiment of the present invention, the oxygen delivery apparatus may be operated using a prescription flow ($Q_p$) and a desired oxygen saving ratio (SR) while maintaining $FIO_2$ equivalency which is similar to that in the conventional CFO method, thereby implementing an oxygen delivery pattern which can be capable of providing comfort to the recipient.

The prescription flow ($Q_p$) may be an oxygen flow which has been prescribed by a doctor and may mean a CFO-based flow (expressed in, for example, liter/min) required to secure appropriate level of $FIO_2$ according to the lesion of the recipient and means an oxygen delivery flow based on doctor's prescription. The prescription flow may be input by the recipient to whom oxygen will be delivered to the oxygen delivery apparatus via a suitable user interface. Also, the oxygen saving ratio (SR) may also be input to the oxygen delivery apparatus via a suitable user interface by the recipient. The oxygen saving ratio (SR) is defined as a ratio ($Q_p/Q_s$) of the prescription flow ($Q_p$) and an average delivery flow ($Q_s$). The average delivery flow ($Q_s$) is an average value of oxygen deliver flow for one period of a respiration, i.e., one inhalation and one exhalation. In the present invention, the oxygen delivery apparatus does not deliver just the prescription flow but delivers the oxygen delivery flow reduced from the prescription flow so as to save oxygen. The oxygen saving ratio (SR) indicates how much the oxygen saved. If the oxygen saving ratio becomes larger, the more oxygen is saved. For example, if the prescription flow ($Q_p$) is 3 lpm (liter per minute) and the saving ratio (SR) is 3, the average delivery flow is 1 lpm. For example, the saving ratio (SR) may be a value between 1 to 6. The recipient may select the saving ratio (SR) from the given range or the given values and may input the selected saving ratio (SR) to the oxygen delivery apparatus. The average delivery flow can be calculated from the input prescription flow and the input saving ratio.

The control unit 40 controls the operation of the outlet valve unit 20 on the basis of the pressure signal transmitted from the pressure sensor 30 and an oxygen delivery mode selected among a plurality of predetermined oxygen delivery modes.

Here, the control unit 40 receives the prescription flow ($Q_p$) that is an oxygen delivery flow prescribed to the recipient and the saving ratio (SR). The control unit 40 selects the oxygen delivery mode from the plurality of oxygen delivery modes depending on comparison of the input saving ratio to a plurality of preset saving ratio, and controls the outlet valve unit 20 to deliver oxygen according to the selected oxygen delivery mode.

Meanwhile, the control unit 40 estimates the breathing pressure of the recipient depending on time on the basis of the pressure signal of the pressure sensor 30 to calculate a breathing pattern and corrects the obtained breathing pattern when an oxygen delivery is controlled. For example, the control unit 40 may grasp a particular point of time (for example, a highest-inhalation pressure time, an exhalation start time, a lowest-exhalation pressure time, etc.) using the pressure actually detected when an oxygen delivery is controlled. When the grasped time is different from a time corresponding to the estimated breathing pattern, the control unit may shift the estimated breathing pattern by a gap of the time difference to correct the estimated breathing pattern. By correcting the breathing pattern in the controlling process and by performing a controlling based on the corrected breathing pattern, it is possible to deliver more accurate flow of oxygen.

The plurality of preset saving ratios may include a lower limit, an upper limit, a first saving ratio which is greater than the lower limit, a second saving ratio which is greater than the first saving ratio and less than the upper limit. The control unit 40 may select the oxygen delivery mode based on the comparison of the input saving ratio with these preset saving ratios. Here, the lower limit of the saving ratio may "1". When the saving ratio is less than or equal to "1" that is the lower limit of the saving ratio, the oxygen delivery mode may be the conventional CFO method, and when the saving ratio is greater than the upper limit, the oxygen delivery mode may be the conventional DOD method. For example, the upper limit may be set to 3.8.

The control unit 40 may select one among the plurality of oxygen delivery modes according to the range of the first saving ratio or the second saving ratio to which the input saving ratio pertains. Here, the first saving ratio and the second saving ratio have the value between the lower limit and the upper limit of the saving ratio. For example, if the input saving ratio is greater than the lower limit of the saving ratio and less than or equal to the first saving ratio, the control unit may select a first oxygen delivery mode may be selected, if the input saving ratio is greater than the first saving ratio and less than or equal to the second saving ratio, the control unit may select a second oxygen delivery mode. And, if the input saving ratio is greater than the second saving ratio and less than or equal to the upper limit of the saving ratio, the control unit may select the third oxygen delivery mode. At this time, for example, the first saving ratio may be set to 1.7 and the second saving ratio may be set to 3.3.

Figure 4:
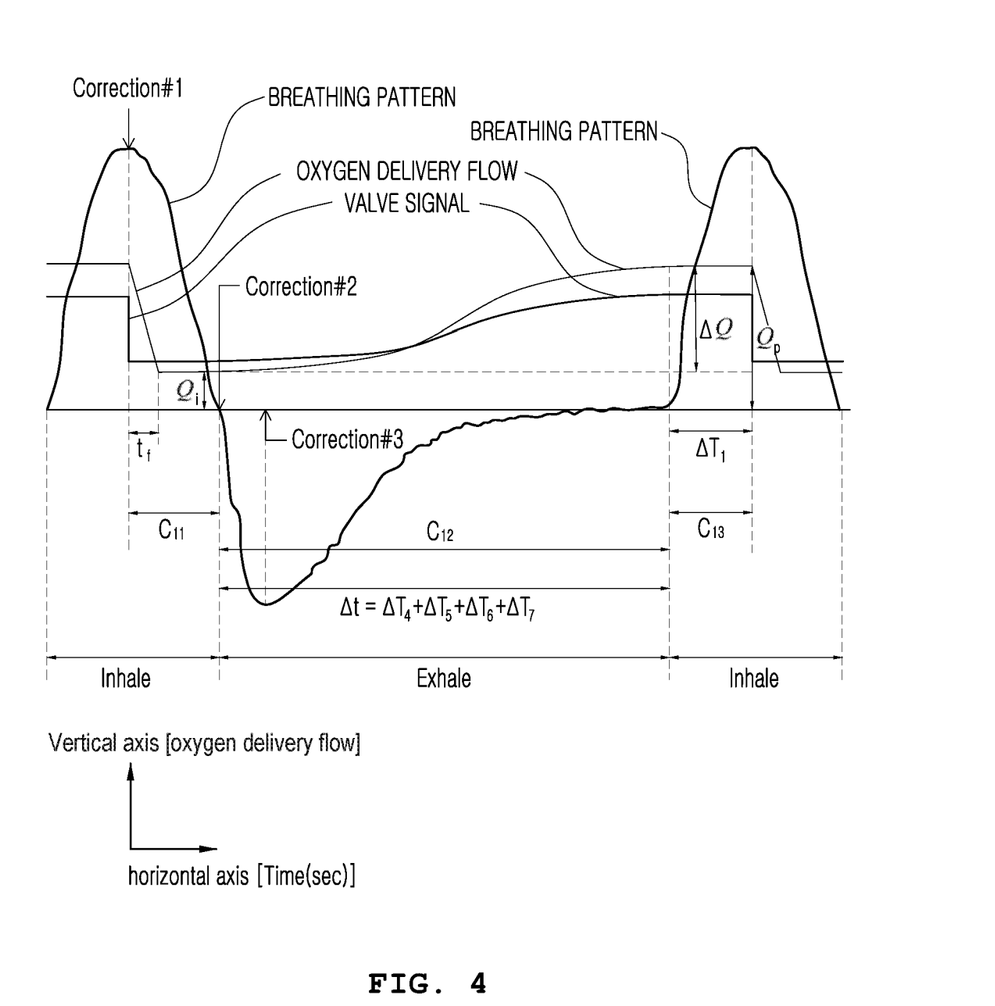
FIGS. 4 to 6 are views for illustrating the first to third oxygen delivery modes in the oxygen delivery method according to an embodiment of the present invention.

Hereinafter, a method of estimating a breathing pattern will be described with reference to FIG. 3 and the first to third oxygen delivery modes will be described in detail with reference to FIGS. 4 to 6.

Referring to FIG. 3, the estimated breathing pattern for a period can be derived through a parameter linear model indicated by a dotted line. The estimated breathing pattern may be derived in a similar manner to a real time breathing pattern. Here, as shown in FIG. 3, the breathing pattern can be estimated using 9 parameters, which include an inhalation start time (t0), a time (t1) at which an inhalation pressure is highest (hereinafter, referred to as "highest-inhalation pressure time), a highest-inhalation pressure (PH), an inhalation end time (t2), an exhalation start time (t3), a time (t4) at which an exhalation pressure is lowest (hereinafter, referred to as: lowest-exhalation pressure time), a lowest-exhalation pressure (PL), a time taken to reach 25% of the lowest-exhalation pressure (t5), and an exhalation end time (t6). For example, the highest-inhalation pressure time and the lowest-exhalation pressure time may be actually derived on the basis of the pressure signal detected by the pressure sensor 30.

At this time, the calculated breathing pattern may be derived on the basis of the parameters calculated by applying weights to the parameters extracted from the previous breathing pattern. For example, the breathing pattern may be derived by the parameters calculated by applying weights to the parameters extracted from three previous breathing patterns. For example, a weight of 0.5 is assigned to a parameter of a breathing pattern of an immediately previous period, a weight of 0.3 is further assigned to a parameter of a breathing pattern of the next previous period, a weight of 0.2 is further assigned to a parameter of a breathing pattern of a previous period of the next previous period, and three (3) parameters to which the weights are assigned are summed and used as parameters of the estimated breathing pattern. Weights are applied in such a manner to obtain nine (9) parameters, thereby determining six (6) places indicated by the symbol "◆". The breathing pattern for a period is derived by connecting the determined six (6) places and the inhalation start time t7 of the next period. In this case, a section ① is an inhale period, a section ② is a rest period, and a section ③ is an exhale period.

In the above-described manner, an upcoming breathing pattern can be estimated using parameters of the previous breathing periods, and the oxygen delivery modes that will be described below can be controlled based on the estimated breathing pattern.

In addition, while controlling of the oxygen delivery mode is performed, correction of the breathing pattern can be performed in real time. During the controlling, the correction of the breathing pattern can be performed at a predetermined time using the breathing pressure detected by the pressure sensor 30 in real time. For example, the correction of the breathing pattern may be performed at the highest-inhalation pressure time, the inhalation end time and the lowest-exhalation pressure time, which are detected in real time. The breathing pattern can be corrected by shifting the corresponding parameters of the breathing pattern based on the real-time pressure at the corresponding time.

First, the oxygen delivery control based on the first oxygen delivery mode will be described with reference to FIG. 4. Among the aforementioned first to third oxygen delivery modes, the first oxygen delivery mode has the lowest saving ratio. FIG. 4 illustrates an oxygen delivery flow controlled using a proportional control valve. In FIG. 4, the vertical axis indicates the oxygen delivery flow and the horizontal axis indicates time. And, the valve signal for controlling the proportional control valve and the flow of oxygen discharged according to the valve signal are shown. The valve signal and the oxygen flow according to the valve signal may be stored in a look-up table as preset values according to the size of a relevant valve. Meanwhile, when the oxygen delivery flow is variably controlled by a combination of a plurality of on-off valves, the on-off valves may be controlled such that the oxygen delivery flow becomes one which is most similar to a target oxygen delivery flow among flows obtained by the combination of a plurality of on-off valves.

The control unit 40 sequentially performs first to third control processes C11, C12 and C13.

First, the first control process C11 starts from the highest-inhalation pressure time in which inhalation is under way, and the control unit 40 is in a control process of the outlet valve unit 20 to deliver oxygen of the input prescription flow from a time prior to the highest-inhalation pressure time up to a time at which the inhalation pressure reaches the highest value.

In the first control process C11, the control unit 40 controls the outlet valve unit 20 using a valve signal that makes the oxygen delivery flow become equal to the base flow at the highest-inhalation pressure time detected in real time in a state in which it controls the outlet valve unit 20 to deliver oxygen of the input prescription flow during inhalation, and controls the state to be maintained up to the exhalation start time. That is to say, the outlet valve unit 20 is controlled by the predetermined valve signal that makes the oxygen delivery flow become equal to the base flow. In this case, as shown in FIG. 4, there is a time difference ($t_f$) between a start time of the valve signal and a time at which the oxygen delivery flow becomes equal to the base flow because there exist a transition period in which the oxygen delivery flow decreases from the prescription flow to the base flow after the outlet valve unit 20 is operated by a valve control signal, and the time difference is an intrinsic value which can be experimentally determined using the corresponding valve. Accordingly, as shown in FIG. 4, the outlet valve unit 20 is controlled by the valve signal at the highest-inhalation pressure time to make the oxygen delivery flow become equal to the base flow. Due to the above, the actually oxygen delivery flow gradually decreases from the prescription flow and reaches the target base flow after the lapse of the transition period ($t_f$), and this state is maintained up to the exhalation start time.

Then, in the second control process C12, the control unit 40 controls the outlet valve unit 20 such that the oxygen delivery flow gradually increases from the base flow to the prescription flow for a period ranging from the exhalation start time to the next inhalation start time.

At this time, the oxygen delivery flow may be controlled to gradually increase along an S-shaped curve. The S-shaped curve is also called as a logistic function and is typically used for indicating a growth curve. For example, the logistic function can be represented by an equation $f(t)=k/1-e^{-a \cdot b}$. Here, the shape of the curve may be determined by appropriately selecting the parameters "a" and "b", and may have a value nearly close to 0 when "t" approaches zero (0) and may be converged to "k" as the value of "t" is increased.

As described above, the oxygen delivery flow is made to gently increase along the S-shaped curve from the exhalation start time to the inhalation start time, thereby minimizing patient's inconvenience while delivering oxygen of the prescription flow at the inhalation start time.

At this time, the base flow may be calculated as a value that makes an average flow of oxygen delivered for one breathing period become equal to the calculated average delivery flow. In detail, the average flow of oxygen delivered may be calculated by dividing a total flow for one breathing period by one period time. Here, total flow may be obtained by adding a flow delivered during a transition period in which a flow actually delivered by the operation of the outlet valve unit in the second control process gradually decreases from the input prescription flow to the base flow. Accordingly, a more accurate flow control can be achieved.

In the third control process C13, the control unit 40 controls the outlet valve unit 20 to allow oxygen of the input prescription flow ($Q_p$) to be delivered from the next inhalation start time to the next highest-inhalation pressure time. As shown in FIG. 4, in the third control process C13, the proportional control valve 23 may be controlled by the valve signal for delivering oxygen of the prescription flow ($Q_p$). Accordingly, the oxygen delivery flow corresponding to the prescription flow ($Q_p$) is delivered.

In the process of executing the above control processes, a correction of the breathing pattern is performed at a plurality of times (Correction #1, #2, #3), and the oxygen delivery flow can be controlled on the basis of the corrected breathing pattern. The correction of breathing pattern may be performed in the manner as described above. For example, the correction of breathing pattern can be performed at a correction time (Correction #1) which is the time at which the inhalation pressure is highest, at a correction time (Correction #2) which is the time at which the exhalation is initiated, and at a correction time (Correction #3) which is the time at which the exhalation pressure is lowest. The control unit 40 can calculate the base flow on the basis of the breathing pattern corrected at the time at which the inhalation pressure is highest to perform the first control process and can correct the breathing pattern again at the time at which the exhalation is initiated to calculate the base flow on the basis of the corrected breathing pattern. And, the control unit can perform the second control process using the calculated base flow. In the process of executing the second control process, in addition, the control unit 40 can correct the breathing pattern again at the time at which the exhalation pressure is lowest, and correct the base flow again on the basis of the corrected breathing pattern to perform the remaining steps of the second control process using the corrected base flow.

The first oxygen delivery mode can be executed by obtaining the base flow in the above-described manner, which can be expressed in the following equation.

First, the base flow is calculated on the basis of the breathing pattern corrected at the correction time (Correction #1) and the first control process is performed on the basis of the calculated base flow. Here, the base flow can be calculated using a relation indicating that the average consumed flow for a breathing period is equal to the calculated average delivery flow ($Q_s$).

The average consumed flow can be calculated using below equation.

(Average consumed flow)=(Total volume)/(Total time)=(Graph area)/(One period time)    [Equation 1]

Here, the relation of "(Graph area)/(One period time)" being equal to the average delivery flow is represented by the following equation.

$$\frac{[Q_{i,1}t_{tot,1} + 0.5(Q_P - Q_{i,1})t_f + 0.5(Q_P - Q_{i,1})\Delta t_1 + (Q_P - Q_{i,1})\Delta T_{1,1}]}{t_{tot,1}} = Q_s \quad \text{[Equation 2]}$$

where $Q_{1,i}$ is the base flow corrected at Correction #1", $t_{tot,1}$ is a breathing period corrected at "Correction #1", $t_f$ is a transition time required for decreasing the valve flow from the prescription flow to the base flow, $\Delta t_1$ is a flow increasing time corrected at "Correction #1" (that is, a time ranging from the exhalation start time to the next inhalation start time), and $\Delta T_{1,1}$ is a time ranging from the inhalation start time corrected at "Correction #1" to the highest-inhalation pressure time.

Equation (2) can be rewritten for the base flow, as represented by Equation 3.

$$Q_{i,1} = \frac{Q_s t_{tot,1} - Q_P(0.5t_f + 0.5\Delta t_1 + \Delta T_{1,1})}{t_{tot,1} - 0.5t_f - 0.5\Delta t_1 - \Delta T_{1,1}} \quad \text{[Equation 3]}$$

Then, the correction is further performed again at "Correction #2", the base flow is again calculated on the basis of the obtained breathing pattern, and the second control process is then performed. Here, the base flow can be calculated in the same manner as described above.

Therefore, the base flow calculated at "Correction #2" is given by Equation 4.

$$Q_{i,2} = \frac{Q_s t_{tot,2} - Q_P(0.5t_f + 0.5\Delta t_2 + \Delta T_{1,2})}{t_{tot,2} - 0.5t_f - 0.5\Delta t_2 - \Delta T_{1,2}} \quad \text{[Equation 4]}$$

where $Q_{i,2}$ is the base flow corrected at "Correction #2", $t_{tot,2}$ is a breathing period corrected at "Correction #2", $t_f$ is a transition time required for decreasing the valve flow from the prescription flow to the base flow, $\Delta t_2$ is a flow increasing time corrected at "Correction #2" (that is, a time ranging from the exhalation start time to the next inhalation start time), and $\Delta T_{1,2}$ is a time ranging from the inhalation start time corrected at "Correction #2" to the highest-inhalation pressure time.

Accordingly, in the second control process, the flow is gradually increased from the base flow ($Q_{i,2}$) corrected at "Correction #2".

Then, corrected parameters are obtained by correcting again the breathing pattern at a time "Correction #3". The control unit 40 performs the second control process up to the next inhalation start time calculated by the breathing pattern corrected at "Correction #3", and then controls the outlet valve unit 20 to allow oxygen of the prescription flow to be delivered from the calculated next inhalation start time to the next highest-inhalation pressure time.

Next, the control unit 40 controls the outlet valve unit 20 to allow oxygen of the prescription flow to be delivered from the next inhalation start time calculated by the by the breathing pattern corrected at "Correction #3" to the highest-inhalation pressure time.

The control unit 40 controls oxygen delivery while repeatedly performing the above-described controlling processes.

Next, the oxygen delivery control according to the second oxygen delivery mode will be described with reference to FIG. 5. Among the aforementioned first to third oxygen delivery modes, the second oxygen delivery mode has an intermediate saving ratio.

The control unit 40 sequentially performs the first to third control processes C21, C22 and C23.

First, the first control process C21 starts from the highest-inhalation pressure time in which inhalation is under way, and the control unit 40 is in a control process of the outlet valve unit 20 to deliver oxygen of the input prescription flow from a time prior to the highest-inhalation pressure time up to the highest-inhalation pressure time.

In the first control process C21, the control unit 40 controls the outlet valve unit 20 using a valve signal that prevents oxygen from being delivered at the highest-inhalation pressure time detected in real time in a state in which it controls the outlet valve unit 20 to deliver oxygen of the input prescription flow during inhalation, and controls the state to be maintained up to the oxygen delivery resumption time ($t_0$). In this case, as shown in FIG. 5, there is a time difference ($t_f$) between a start time of the valve signal and a time at which the oxygen delivery flow becomes "0" because there exist a transition period in which the oxygen delivery flow decreases from the prescription flow to "0" after the outlet valve unit 20 is operated by a valve control signal, and the time difference ($t_f$) is an intrinsic value empirically determined using the corresponding valve. Accordingly, as shown in FIG. 5, the outlet valve unit 20 is controlled at the highest-inhalation pressure time using the valve signal that makes the oxygen delivery flow become "0". Accordingly, the actually oxygen delivery flow gradually decreases from the prescription flow to reach the target flow "0" after the lapse of the transition period ($t_f$), and this state is maintained up to the oxygen delivery resumption time.

Then, in the second control process C22, the control unit 40 controls the outlet valve unit 20 such that the oxygen delivery flow gradually increases from "0" to the prescription flow for a period ranging from the oxygen delivery resumption time ($t_0$) to the next inhalation start time. Here, like in the first control mode, the oxygen delivery flow may be controlled to gradually increase along an S-shaped curve.

At this time, the oxygen delivery resumption time can be calculated as a time in which the average flow of oxygen delivered for a breathing period becomes equal to the calculated average delivery flow. For example, the average flow of oxygen delivered may be calculated by dividing a total flow for a breathing period by one period time. At this time, the total flow may be obtained by adding a flow delivered during a transition period in which a flow actually delivered by the operation of the outlet valve unit 20 in the first control process gradually decreases from the input prescription flow to "0". Accordingly, a more accurate flow control can be achieved.

In the third control process C23, the control unit 40 controls the outlet valve unit 20 to allow oxygen of the input prescription flow ($Q_p$) to be delivered from the next inhalation start time to the next highest-inhalation pressure time. As shown in FIG. 5, in the third control process C23, the proportional control valve 23 may be controlled by a valve signal for delivering oxygen of the prescription flow ($Q_p$). Accordingly, the oxygen delivery flow corresponding to the prescription flow ($Q_p$) is delivered.

While the aforementioned controlling processes are performed, correction of a breathing pattern may be performed at a plurality of points of time (Correction #1, #2, #3), and the oxygen delivery flow can be controlled based on the corrected breathing pattern. For example, like in the first control mode, the correction of the breathing pattern may be performed at the highest-inhalation pressure time (Correction #1), the exhalation start time (Correction #2), and the lowest-exhalation pressure time (Correction #3). Accordingly, the control unit 40 may perform the third control process on the basis of parameters of the breathing pattern obtained by the correction performed at the lowest-exhalation pressure time (Correction #3).

The second oxygen delivery mode can be executed in the above-described manner, and content of the second oxygen delivery mode and a method of obtaining the oxygen delivery resumption time will now be described.

First, the control unit 40 controls the outlet valve unit 20 such that the oxygen delivery flow becomes "0" at the highest-inhalation pressure time detected in real time. That is to say, the outlet valve unit 20 is controlled to be closed at the highest-inhalation pressure time. The breathing pattern may be corrected at the highest-inhalation pressure time.

Then, the breathing pattern is again corrected at the exhalation start time ("Correction #2"), and the oxygen delivery resumption time may be obtained on the basis of the breathing pattern corrected at the exhalation start time. Here, the oxygen delivery resumption time can be calculated using a relationship indicating that the average consumed flow for a breathing period is equal to the calculated average delivery flow ($Q_s$).

Figure 5:
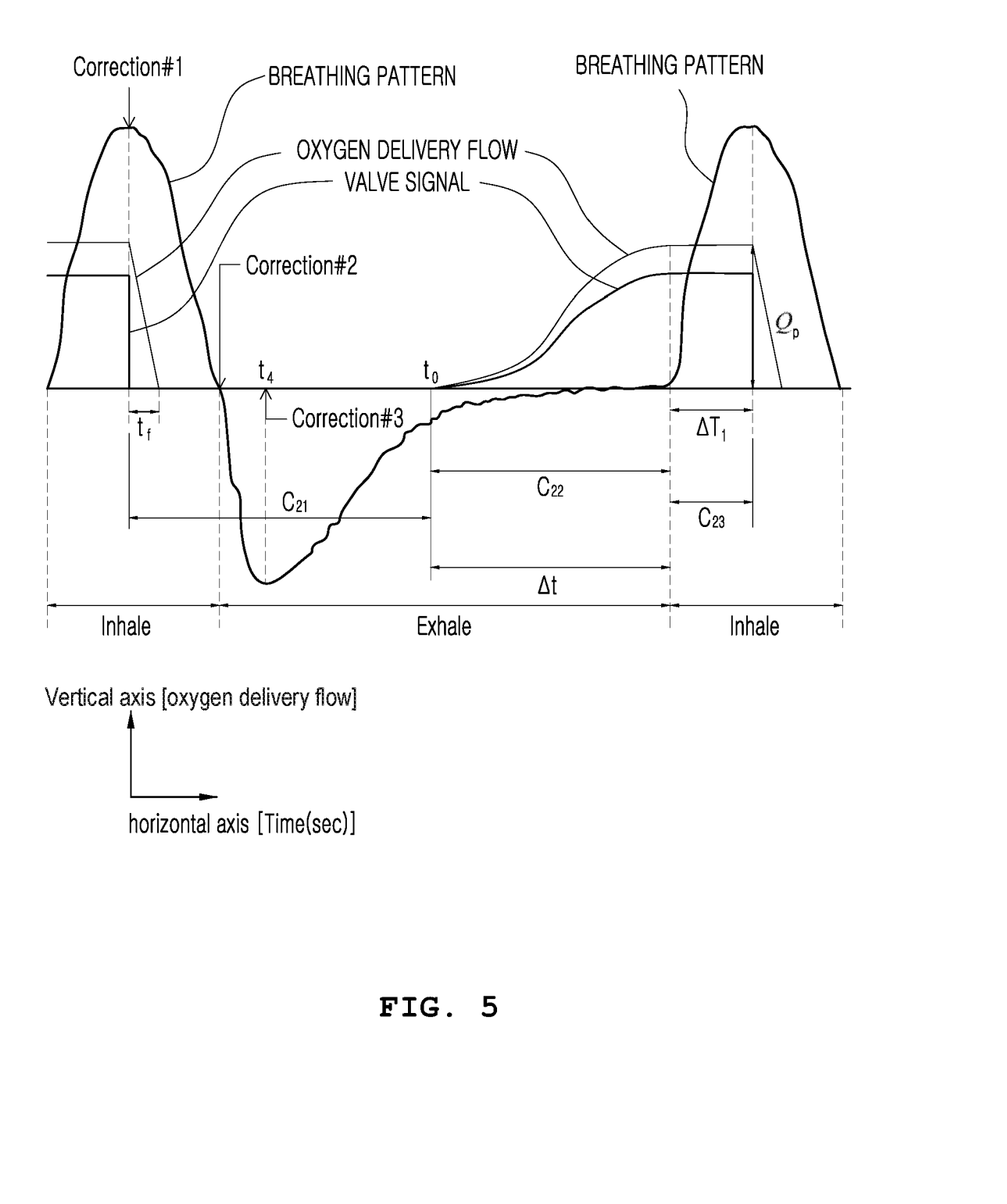

First, Equations 1 and 2 for obtaining the average consumed flow may be applied to a case shown in FIG. 5, giving Equation 5.

$$\frac{[0.5Q_p t_f + 0.5Q_p \Delta t_2 + Q_p \Delta T_{1,2}]}{t_{tot,2}} = Q_s \quad \text{[Equation 5]}$$

Where, $t_{tot,2}$ is a breathing period corrected at "Correction #2", $t_f$ is a transition time required for decreasing the oxygen delivery flow from the prescription flow to "0", $\Delta t_2$ is a flow increasing time corrected at "Correction #2" (that is, a time ranging from the oxygen delivery resumption time ($t_0$) to the next inhalation start time), and $\Delta T_{1,2}$ is a time ranging from the inhalation start time corrected at "Correction #2" to the next highest-inhalation pressure time.

Equation 5 can be rewritten for the flow increasing time ($\Delta t_2$), as represented by Equation 6.

$$\Delta t_2 = \frac{Q_s t_{tot,2} - 0.5Q_p t_f - Q_t \Delta T_{1,2}}{0.5Q_p} \quad \text{[Equation 6]}$$

The oxygen delivery resumption time ($t_0$) may be calculated by subtracting the flow increasing time ($\Delta t_2$) from the next inhalation start time obtained from the corrected breathing pattern.

The control unit 40 may compare the thus obtained oxygen delivery resumption time ($t_0$) with the lowest-exhalation pressure time ($t_4$) obtained from the breathing pattern corrected at "Correction #2", and as the result of the comparing, if it is determined that the oxygen delivery resumption time ($t_0$) precedes the lowest-exhalation pressure time ($t_4$), oxygen delivery may be resumed at the obtained oxygen delivery resumption time ($t_0$), that is, at a start time of the second control process.

However, as the result of comparing the obtained oxygen delivery resumption time ($t_0$) with the lowest-exhalation pressure time ($t_4$) obtained from the breathing pattern corrected at "Correction #2", when it is determined that the oxygen delivery resumption time ($t_0$) follows the lowest-exhalation pressure time ($t_4$), the control unit 40 corrects again the breathing pattern at Correction #3 that is a correction time of the lowest-exhalation pressure time ($t_4$), and the oxygen delivery resumption time is again obtained based on the corrected breathing pattern to resume oxygen delivery from the obtained oxygen delivery resumption time (that is, a start time of the second control process).

The obtaining of the oxygen delivery resumption time based on the breathing pattern corrected at "Correction #3" can be performed in a similar manner as described above. The relationship indicating that the average consumed flow is equal to the calculated average delivery flow ($Q_s$) can be represented in Equation 7, similar to Equation 5.

$$\frac{[0.5Q_p t_f + 0.5Q_p \Delta t_3 + Q_p \Delta T_{1,3}]}{t_{tot,3}} = Q_s \qquad \text{[Equation 7]}$$

Where, $t_{tot,3}$ is a breathing period corrected at "Correction #3", $t_f$ is a transition time required for decreasing the oxygen delivery flow from the prescription flow to reach "0", $\Delta t_3$ is a flow increasing time corrected at "Correction #3" (that is, a time ranging from the oxygen delivery resumption time ($t_0$) to the next inhalation start time), and $\Delta T_{1,3}$ is a time ranging from the inhalation start time corrected at "Correction #3" to the next highest-inhalation pressure time.

Equation 7 can be rewritten for the flow increasing time, as represented by Equation 8.

$$\Delta t_3 = \frac{Q_s t_{tot,3} - 0.5Q_p t_f - Q_p \Delta T_{1,3}}{0.5Q_p} \qquad \text{[Equation 8]}$$

The oxygen delivery resumption time ($t_0$) may be obtained by subtracting the flow increasing time ($\Delta t_3$) obtained by Equation (8) from the next inhalation start time obtained from the corrected breathing pattern.

The control unit 40 may compare the oxygen delivery resumption time ($t_0$) obtained again at the lowest-exhalation pressure time with the lowest-exhalation pressure time ($t_4$). As the result of the comparing, when it is determined that the oxygen delivery resumption time ($t_0$) precedes the lowest-exhalation pressure time ($t_4$), the control unit 40 may control the outlet valve unit 20 to immediately resume oxygen delivery at the lowest-exhalation pressure time, and when the oxygen delivery resumption time ($t_0$) follows the lowest-exhalation pressure time, the control unit 40 may control the outlet valve unit 20 such that a state in which oxygen delivery is not performed is maintained and oxygen delivery is then resumed at the obtained oxygen delivery resumption time (that is, at a start time of the second control process).

The control unit 40 performs the second control process by controlling oxygen delivery to be resumed at the oxygen delivery resumption time and then gradually increasing the oxygen delivery flow to reach the prescription flow up to the next inhalation start time.

Next, the control unit 40 performs the third control process by controlling oxygen to be continuously delivered at the same flow with the prescription flow from the next inhalation start time to the next highest-inhalation pressure time.

The oxygen delivery control according to the third oxygen delivery mode will now be described with reference to FIG. 6. Among the aforementioned first to third oxygen delivery modes, the first oxygen delivery mode has a highest saving ratio.

The control unit 40 controls the outlet valve unit 20, specifically, the proportional control valves 21 and 23 capable of delivering oxygen having a pulse-like flow profile, and the on-off valve 25, thereby executing the third oxygen delivery mode. In FIG. 6, a valve signal 1 is a signal for controlling driving of the proportional control valves 21 and 23, and a valve signal 2 is a signal for controlling driving of the on-off valve 25.

The control unit 40 sequentially performs the first to third control processes C31, C32 and C33.

In the first control process C31, the control unit 40 controls the outlet valve unit 20 to prevent oxygen from being delivered until the oxygen delivery resumption time ($t_0$) during exhalation.

Then, in the second control process C32, the control unit 40 controls the outlet valve unit 20 such that the oxygen delivery flow is made to gradually increase by a constant amount ($\Delta Q$) from "0" to the target oxygen flow. In the second control process, the oxygen delivery flow may be controlled to gradually increase along a S-shaped curve.

Here, the oxygen delivery resumption time may be set to a time that precedes the next inhalation start time by a predetermined time ($\Delta t$). For example, the predetermined time may be set to 0.5 seconds. The target oxygen flow may be obtained as a value that makes an average flow of total oxygen delivered for a period obtained by adding the oxygen delivery flow in the second control process with the oxygen delivery flow in the form of pulses in the third control process become equal to the calculated average delivery flow.

Next, in the third control process C33, the control unit 40 controls the outlet valve unit 20 to deliver oxygen having a pulse-like flow profile at the inhalation start.

While the aforementioned controlling processes are performed, correction of a breathing pattern may be performed at a plurality of points of time (Correction #1, #2, #3), and the oxygen delivery flow can be controlled based on the corrected breathing pattern. For example, like in the first control mode, the correction of the breathing pattern may be performed at the highest-inhalation pressure time (Correction #1), the exhalation start time (Correction #2), and the lowest-exhalation pressure time (Correction #3). Accordingly, the control unit 40 may perform the second control process on the basis of parameters of the breathing pattern corrected at the lowest-exhalation pressure time (Correction #3).

The third oxygen delivery mode can be executed in the above-described manner, and content of the third oxygen delivery mode and a method for calculating the oxygen delivery resumption time will now be described.

First, in the first control process, the control unit 40 controls the outlet valve unit 20 to prevent oxygen from being delivered during exhalation. As shown in FIG. 6, at this time, oxygen delivery may not be performed from the highest-exhalation pressure time that is a start time of a breathing period to a start time of the second control process.

The breathing pattern is corrected at the lowest-exhalation pressure time (Correction #3), and the oxygen delivery resumption time may obtain the target oxygen flow using the next inhalation start time, which is one of parameters of the corrected breathing pattern.

Here, the target oxygen flow of the second control process can be obtained using a relationship indicating that that the average consumed flow for a breathing period is equal to the calculated average delivery flow ($Q_s$).

Figure 6:
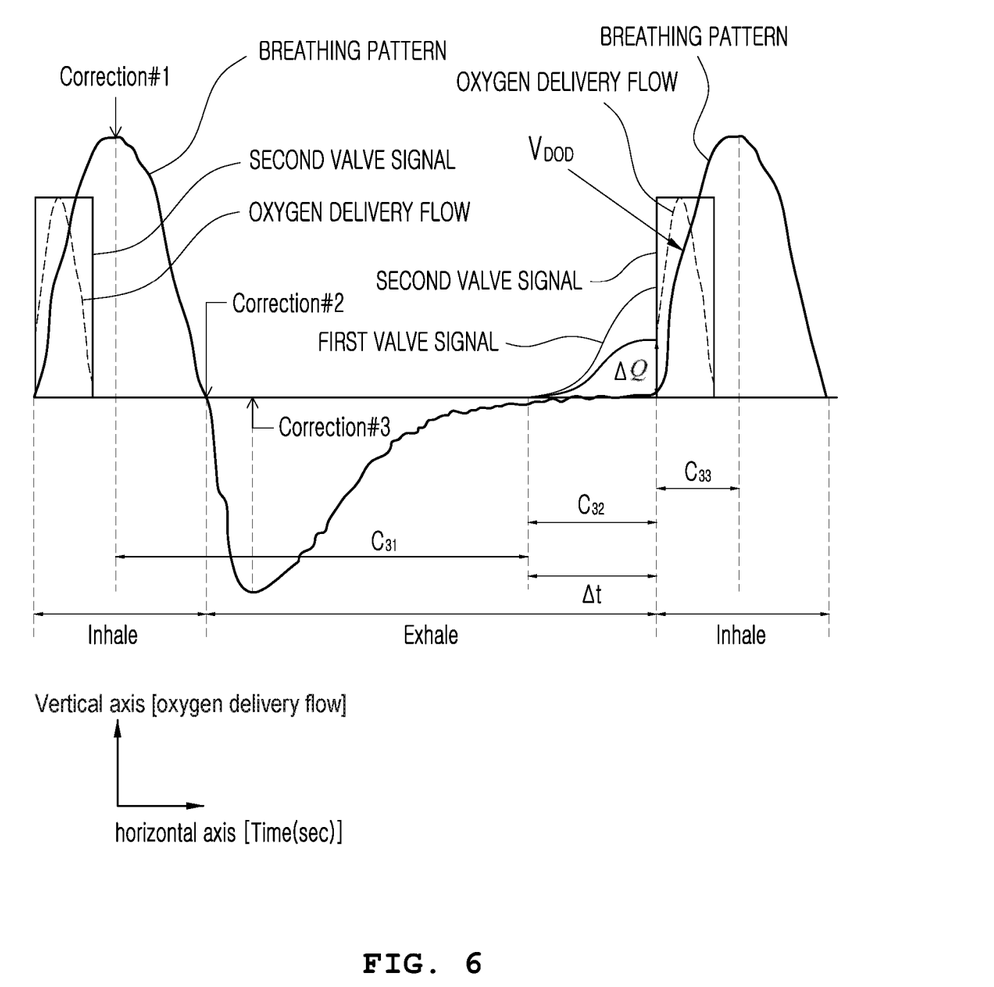

Equations 1 and 2 for obtaining the average consumed flow may be applied to a case shown in FIG. 6, giving Equation 9.

$$\frac{[V_{DOD} + 0.5\Delta t \Delta Q]}{t_{tot,3}} = Q_s \qquad \text{[Equation 9]}$$

where $t_{tot,3}$ is a breathing period corrected at "Correction #3", $\Delta t$ is a predetermined value (e.g., 0.5 sec) as a time difference between the next inhalation start time corrected at "Correction #3" and the oxygen delivery resumption time, $V_{DOD}$ is a volume of pulse-like oxygen delivered through the on-off valve 25 (i.e., a value set according to the prescription flow), and $\Delta Q$ is an increment of the oxygen delivery flow required to increase from "0" to the target oxygen flow in the second control process (i.e., a value that makes the target oxygen flow become equal to $\Delta Q$). Here, $V_{DOD}$ is appropriately selected in consideration of the magnitude of the prescription flow and is generally set to be slightly smaller than the oxygen volume determined by the demand oxygen delivery method.

Equation 9 can be rewritten for the increment ($\Delta Q$) of the oxygen delivery flow, as represented by Equation 10.

$$\Delta Q = \frac{Q_s t_{tot,3} - V_{DOD}}{0.5\Delta t} \qquad \text{[Equation 10]}$$

Since the target oxygen flow is equal to the increment of the target oxygen delivery flow, it can be obtained using Equation 10.

As described above, in the second control process, the oxygen delivery flow is made to gradually increase from the oxygen delivery resumption time to reach the target oxygen flow at the next inhalation start time. Here, the control unit 40 outputs the valve signal 1 to control driving of the proportional control valves 21 and 23, thereby allowing the oxygen delivery flow to gradually increase in the second control process.

Then, the control unit 40 performs the third control process by controlling oxygen having a pulse-like flow profile to be delivered at the inhalation start time. Here, the control unit 40 outputs the valve signal 2 to control driving of the on-off valve 25, thereby allowing the oxygen having a pulse-like flow profile to be delivered in the third control process.

According to the embodiment of the present invention, the proportional control valves 21 and 23 is controlled to allow the same flow oxygen to be continuously delivered, thereby implementing the conventional CFO method and only the on-of valve is driven to allow oxygen having a pulse-like flow profile to be delivered, thereby implementing the conventional DOD method.

Although the foregoing embodiments have been described to practice the oxygen delivery apparatus and method according to the present invention, these embodiments are set forth for illustrative purposes and do not serve to limit the invention. Those skilled in the art will readily appreciate that many modifications and variations can be made, without departing from the spirit and scope of the invention as defined in the appended claims, and such modifications and variations are encompassed within the scope and spirit of the present invention.

What is claimed is:

1. An oxygen delivery apparatus comprising:
an oxygen tank storing oxygen;
an outlet valve unit configured to include a variable flow valve capable of variably controlling an amount of oxygen delivered from the oxygen tank to a recipient;
a pressure sensor adapted to detect a breathing pressure of the recipient and outputting a pressure signal corresponding to the breathing pressure; and
a control unit controlling an operation of the outlet valve unit based on the pressure signal from the pressure sensor to control the amount of oxygen delivered to the recipient,
wherein the control unit selects an oxygen delivery mode among a plurality of preset oxygen delivery modes based on a saving ratio (SR), the saving ratio being input by the recipient and being a ratio of a prescription flow ($Q_p$) and an average delivery flow ($Q_s$), and controls the outlet valve unit based on the pressure signal and the selected oxygen delivery mode.

2. The oxygen delivery apparatus of claim 1, wherein the control unit selects the oxygen delivery mode depending on comparison of the input saving ratio to a plurality of preset saving ratios.

3. An oxygen delivery method using an oxygen delivery apparatus comprising:
an oxygen tank storing oxygen;
an outlet valve unit configured to include a variable flow valve capable of variably controlling an amount of oxygen delivered from the oxygen tank to a recipient;
a pressure sensor adapted to detect a breathing pressure of the recipient and outputting a pressure signal corresponding to the breathing pressure; and
a control unit controlling an operation of the outlet valve unit based on the pressure signal from the pressure sensor to control the amount of oxygen delivered to the recipient,
wherein an oxygen delivery mode is selected among a plurality of preset oxygen delivery modes based on a saving ratio (SR), the saving ratio being input by the recipient and being a ratio of a prescription flow ($Q_p$) and an average delivery flow ($Q_s$), and the outlet valve unit is controlled based on the pressure signal and the selected oxygen delivery mode,
wherein the oxygen delivery mode is selected depending on comparison of the input saving ratio to a plurality of preset saving ratios.

4. The oxygen delivery method of claim 3, wherein the plurality of preset oxygen delivery modes comprises a first oxygen delivery mode, a second oxygen delivery mode and a third oxygen delivery mode, wherein the plurality of preset saving ratios comprise a first preset saving ratio and a second preset saving ratio which is greater than the first preset saving ratio, and wherein the first oxygen delivery mode is selected if the input saving ratio is less than the first preset saving ratio, the second oxygen delivery mode is selected if the input saving ratio is between the first preset saving ratio and the second preset saving ratio, and the third oxygen delivery mode is selected if the input saving ratio is greater than the second preset saving ratio.

5. The oxygen delivery method of claim 4, wherein in the first oxygen delivery mode a first control process, a second control process and a third control process are sequentially performed, the first control process being performed to control the outlet valve unit for making an oxygen delivery flow become equal to a base flow at highest-inhalation pressure time in a state in which the outlet valve unit is controlled to deliver the prescription flow during inhalation and to control the state to be maintained up to an exhalation start time detected in real time, the second control process being performed to control the outlet valve unit to allow the oxygen delivery flow to gradually increase from the base flow up to the prescription flow for a period from the exhalation start time to the next inhalation start time, and the third control process being performed to control the outlet valve unit to deliver the prescription flow from the next inhalation start time to a next highest-inhalation pressure time.

6. The oxygen delivery method of claim 4, wherein in the second oxygen delivery mode a first control process, a second control process and a third control process are sequentially performed, the first control process being performed to control the outlet valve unit to prevent an oxygen delivery at a highest-inhalation pressure time detected in real time in a state in which the outlet valve unit is controlled to deliver the prescription flow and to control the state to be maintained up to a delivery resumption time, the second control process being performed to control the outlet valve unit to allow the oxygen delivery flow to gradually increase from zero up to the prescription flow for a period from the oxygen delivery resumption time to a next inhalation start time, and the third control process being performed to control the outlet valve unit to deliver the prescription flow from the next inhalation start time to a next highest-inhalation pressure time.

7. The oxygen delivery method of claim 4, wherein the oxygen delivery apparatus further comprises an on-off valve that delivers oxygen having a pulse shape flow profile, and wherein in the third oxygen delivery mode a first control process, a second control process and a third control process are sequentially performed, the first control process being performed to control the outlet valve unit to prevent an oxygen delivery up to an oxygen delivery resumption time during exhalation, the second control process being performed to control the outlet valve unit to gradually increase the oxygen delivery flow up to a target oxygen flow for a period from the oxygen delivery resumption time to a next inhalation start time, and the third control process being performed to control the outlet valve unit to deliver oxygen having a pulse shape flow profile at the next inhalation start time.

8. An oxygen delivery method for delivering oxygen stored in an oxygen tank to a recipient, comprising:

receiving a prescription flow ($Q_p$) that is an oxygen delivery flow prescribed to the recipient;

receiving a saving ratio (SR), the saving ratio being input by the recipient and being a ratio of a prescription flow ($Q_p$) and an average delivery flow ($Q_s$);

selecting an oxygen delivery mode among a plurality of preset oxygen delivery modes based on the saving ratio;

detecting a breathing pressure of the recipient; and controlling an oxygen delivery flow to the recipient based on the prescription flow ($Q_p$), the saving ratio (SR) and detected breathing pressure.

9. The oxygen delivery method of claim 8, wherein the oxygen delivery mode is selected depending on comparison of the input saving ratio to a plurality of preset saving ratios.

10. The oxygen delivery method of claim 9, wherein the plurality of preset oxygen delivery modes comprises a first oxygen delivery mode, a second oxygen delivery mode and a third oxygen delivery mode, wherein the plurality of preset saving ratios comprise a first preset saving ratio and a second preset saving ratio which is greater than the first preset saving ratio, and wherein the first oxygen delivery mode is selected if the input saving ratio is less than the first preset saving ratio, the second oxygen delivery mode is selected if the input saving ratio is between the first preset saving ratio and the second preset saving ratio, and the third oxygen delivery mode is selected if the input saving ratio is greater than the second preset saving ratio.

11. The oxygen delivery method of claim 10, wherein in the first oxygen delivery mode a first control process, a second control process and a third control process are sequentially performed, the first control process being performed to make an oxygen delivery flow become equal to a base flow at highest-inhalation pressure time in a state in which the prescription flow is delivered during inhalation and to control the state to be maintained up to an exhalation start time detected in real time, the second control process being performed to allow the oxygen delivery flow to gradually increase from the base flow up to the prescription flow for a period from the exhalation start time to the next inhalation start time, and the third control process being performed to deliver the prescription flow from the next inhalation start time to a next highest-inhalation pressure time.

12. The oxygen delivery method of claim 10, wherein in the second oxygen delivery mode a first control process, a second control process and a third control process are sequentially performed, the first control process being performed to prevent an oxygen delivery at a highest-inhalation pressure time detected in real time in a state in which the prescription flow is delivered and to control the state to be maintained up to a delivery resumption time, the second control process being performed to allow the oxygen delivery flow to gradually increase from zero up to the prescription flow for a period from the oxygen delivery resumption time to a next inhalation start time, and the third control process being performed to deliver the prescription flow from the next inhalation start time to a next highest-inhalation pressure time.

13. The oxygen delivery method of claim 10, wherein in the third oxygen delivery mode a first control process, second control process and a third control process are sequentially performed, the first control process being performed to prevent an oxygen delivery up to an oxygen delivery resumption time during exhalation, the second control process being performed to gradually increase the oxygen delivery flow up to a target oxygen flow for a period from the oxygen delivery resumption time to a next inhalation start time, and the third control process being performed to deliver oxygen having a pulse shape flow profile at the next inhalation start time.

* * * * *